United States Patent [19]

Hill et al.

[11] 4,122,254

[45] Oct. 24, 1978

[54] PROCESS FOR PREPARING AURANOFIN

[75] Inventors: David T. Hill, North Wales, Pa.; Ivan Lantos, Blackwood, N.J.; Blaine M. Sutton, Hatboro, Pa.

[73] Assignee: SmithKline Corporation, Philadelphia, Pa.

[21] Appl. No.: 811,670

[22] Filed: Jun. 30, 1977

[51] Int. Cl.$^2$ ............................................. C07H 23/00
[52] U.S. Cl. ....................................... 536/121; 536/4; 536/122; 424/180
[58] Field of Search .................................. 536/121, 4

[56] References Cited

U.S. PATENT DOCUMENTS 3,635,945  1/1972  Nemeth et al. ........................... 536/4

OTHER PUBLICATIONS

Sutton et al., J. Med. Chem. 15, 1095 (1972).

*Primary Examiner*—Johnnie R. Brown
*Assistant Examiner*—Blondel Hazel
*Attorney, Agent, or Firm*—William H. Edgerton

[57] ABSTRACT

Auranofin and its congeners are prepared by the reaction of a S-substituted 2,3,4,6-tetra-O-acetyl-1-thio-$\beta$-D-glucopyranose with a tertiary phosphine gold ester or sulfide.

5 Claims, No Drawings

PROCESS FOR PREPARING AURANOFIN

This invention comprises a new chemical method for the preparation of auranofin and its congeners which uses as the key starting material a 2,3,4,6-tetra-O-acetyl-glucopyranosyl thioether or thioester whose aglycone portions (R) is a facile leaving group such as a stabilized carbonium ion or a facile displaceable group such as an acyl group. This ether or ester starting material is reacted with a reactive tertiary phosphine gold ester or sulfide.

Auranofin is an orally active antiarthritic agent which is useful in man [J. Med. Chem. 15 1095 (1972); U.S. Pat. No. 3,635,945]. In these references auranofin is prepared by reacting an alkali metal salt of a 1-thio-$\beta$-D-glucopyranose with a trialkyl phosphine gold halide. The invention claimed here is believed to be quite distinct from such prior art processes and therefore patentable.

The process of this invention is illustrated by the following:

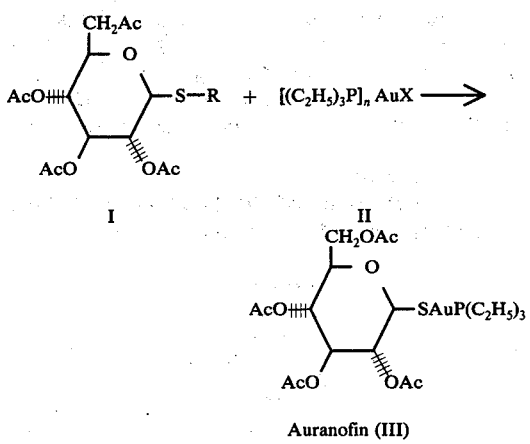

Auranofin (III)

in which
R is a displaceable group which forms either a relatively stable carbonium or ionic leaving group. These may be a substituted or unsubstituted arylmethyl for example, a benzyl, benzhydryl or triphenylmethyl optionally substituted by one or more methoxy groups or a methylenedioxy group; an acyl group such as a substituted or unsubstituted lower alkanoyl of 1–6 carbons for example acetyl, propionyl, butanoyl, benzoyl, trifluoroacetyl, or a lower alkyl of 1–6 carbons activated by $\alpha$-substitution such as by an oxygen atom for example methoxymethyl;

X is a reactive halo for example, chloro, bromo or iodo or, only when R is an acyl group, triethylphosphine goldthio [$(C_2H_5)_3PAuS-$];

$n$ is 1 or 2 and

Ac is acetyl.

Also included in this reaction is a variation which comprises reaction of the thioether (I) with a heavy metal salt such as silver nitrate to give the silver salt of the sugar thiol (III) which is reacted with the tertiary phosphine gold reagent (II) to give auranofin

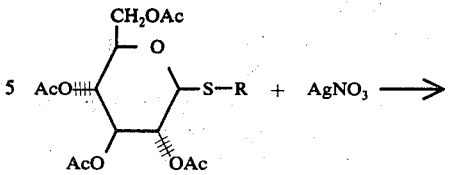

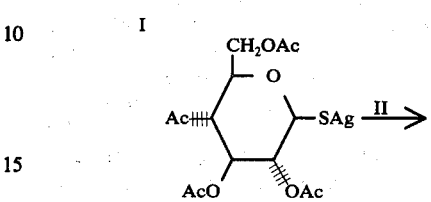

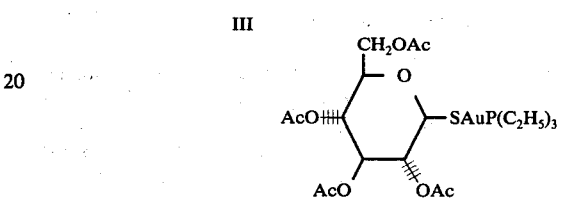

Auranofin

This reaction can be carried out in one step or two. Also the reaction conditions for the reaction described in B may vary from those described hereafter for example a lower alcohol such as methanol or ethanol or another solvent in which the reactants are soluble such as dimethylformamide, dimethylacetamide, acetone or diethylcarbonate may be used.

In the process of this invention (A above) the thioether or thioester reagent (I) reacts very readily with the tertiary phosphine gold reagent (II). Usually the reaction proceeds at about room temperature but temperatures up to the boiling point of the reaction mixture may be used. A preferred range of temperatures is from 25°–75°. The reaction time is until the reaction is complete but may range from one-half hour up to several days depending on the temperature of the reaction and the reactivity of the reagents. Also the tertiary phosphine gold halides are more reactive than the sulfides and are less facile than are the bis tertiary phosphine gold halides.

Generally speaking any aprotic organic solvent in which the reactants are soluble may be used such as a common halogentated hydrocarbon solvent such as chloroform, carbon tetrachloride, ethylene tetrachloride or methylene chloride, a benzenoid solvent such as benzene, toluene or xylene, dimethylformamide, dimethylacetamide, ethereal solvents such as diethyl ether or dioxane, ethylacetate, ethyl carbonate, dimethylsulfoxide, lower alkanols sucnh as methanol, ethanol or isopropanol. The chloro lower hydrocarbons especially methylene chloride are preferred.

The reaction product, auranofin, is isolated by standard methods for example by evaporating the solvent in vacuo if necessary to give crude auranofin which is then purified by chromatography or fractional crystallization. The starting materials are either known or are prepared by reactions detailed in the following illustrative examples. All temperatures are on the Centigrade scale.

EXAMPLE 1

2,3,4,6-Tetra-O-acetyl-L-S-trityl-L-thio-β-D-glucopyranose

A pyridine solution (100 ml) of 35 g (0.096 mole) of 2,3,4,6-tetra-O-acetyl-L-thio-β-D-glucopyranose [Methods in Carbohydrate Chemistry, Vol. 2, page 436 (1967)] and 28 g (0.10 mole) of triphenylmethyl chloride was stirred at room temperature for 12 hours. The solution was then filtered and the pyridine removed at reduced pressure. The residue was dissolved in chloroform (350 ml), washed with water (5 × 100 ml) and the chloroform solution dried (magnesium sulfate). The solvent was removed at reduced pressure and the residual oil dissolved in methanol and cooled to give 17 g (29%) of crystalline 2,3,4,6-tetra-O-acetyl-L-S-trityl-L-thio-β-D-glucopyranose, m.p. 177°–179°; $[\alpha]_D^{25}$ (1% methanol) = −37.8°.

A chloroform solution (50 ml) of 3.0 g (4.9 mmoles) of 2,3,4,6-tetra-O-acetyl-L-S-trityl-L-thio-β-D-glucopyranose and 1.95 g (4.9 mmoles) of bromo(triethylphosphine)gold (I) [Aust. J. Chem. 19, 539 (1966)] was stirred at room temperature for 48 hours and then refluxed for 48 hours. The solvent was removed at reduced pressure and the residue subjected to column chromatography (silica gel/5% ether-chloroform). Crystallization of the resulting crude product from methanol-water gave auranofin as white crystals, m.p. 109°–113°; $[\alpha]_D^{25}$ (1% methanol) = −55.7°.

Substituting stoichiometric quantities of p-methoxybenzyl chloride, benzyl chloride, o,p-dimethoxy-benzyl chloride or p-bromobenzhydryl bromide for triphenylmethyl(trityl) chloride in the above reactions gives auranofin.

EXAMPLE 2

2,3,4,6-Tetra-O-acetyl-L-S-trityl-L-thio-β-D-glucopyranose

A pyridine solution (100 ml) of 35 g (0.096 mole) of 2,3,4,6-tetra-O-acetyl-L-thio-β-D-glucopyranose [Methods in Carbohydrate Chemistry, Vol. 2, 436 (1963)] and 28 g (0.10 mole) of triphenylmethyl chloride was stirred at room temperature for 12 hours. The solution was filtered and the pyridine removed at reduced pressure. The residue was dissolved in chloroform (350 ml), washed with water (5 × 100 ml) and the chloroform solution dried over magnesium sulfate. The solvent was removed at reduced pressure and the residue dissolved in methanol and cooled to give 17 g (29%) of crystalline 2,3,4,6-tetra-O-acetyl-D-S-trityl-L-thio-β-D-glucopyranose, m.p. 177°–179°; $[\alpha]_D^{25}$ (1% methanol) = −37.8°.

A methanol solution (30 ml) of 0.84 g (4.9 mmoles) of silver nitrate and 3.0 g (4.9 mmoles) of 2,3,4,6-tetra-O-acetyl-L-S-trityl-L-thio-β-D-glucopyranose was stirred at 35° for 30 minutes. The solution was then diluted to 100 ml with ether and cooled at −20° overnight. The resulting precipitate was removed by filtration, washed with ether and dried to give 1.94 g (83%) of 2,3,4,6-tetra-O-acetyl-L-S-silver-L-thio-β-D-glucopyranose, m.p. 123°–128°.

A methanol solution (35 ml) of 1.94 g (4.1 mmoles) of 2,3,4,6-tetra-O-acetyl-L-S-silver-L-thio-β-D-glucopyranose and 1.44 g (4.1 mmoles) of chloro(triethylphosphine) gold (I) was stirred at room temperature for 1 hour. The solution was filtered and the solvent removed at reduced pressure. Chromatography of the residue (silica gel/chloroform) followed by crystallization from methanol-water gave auranofin, m.p. 108°–110°; $[\alpha]_D^{25}$ (1% methanol) = −55.8°.

EXAMPLE 3

A chloroform solution (25 ml) of 0.61 g (1.5 mmoles) of 2,3,4,6-tetra-O-acetyl-L-S-acetyl-L-thio-β-D-glucopyranose and 1.0 g (1.5 mmoles) of bis(triethylphosphinegold)sulfide was refluxed overnight and the solvent removed at reduced pressure. Chromatography of the residue (silica gel, benzene-chloroform 0 to 100% gives a yellow oil with the chloroform eluate. Preparative thin layer chromatography (silica gel, ether-2% acetone followed by crystallization from methanol-water gives auranofin, m.p. 110°–111°.

EXAMPLE 4

A chloroform solution (25 ml) of 1.0 g (2.5 mmoles) of pentaacetylthioglucose and 1.15 g (2.5 mmoles) of bistriethylphosphine)gold chloride was stirred at room temperature for 72 hours and the solvent removed at reduced pressure. Chromatography of the residue (silica gel, benzene-chloroform 0 to 100%) gives an oil which was purified further by preparative thin layer chromatography (silica gel, ether-2% acetone). Crystallization from methanol-water gives auranofin, m.p. 98°–101°.

What is claimed is:

1. The method of preparing auranofin comprising reacting a compound of the structure:

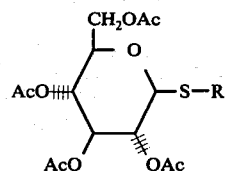

in which Ac is acetyl and R is benzyl, p-methoxybenzyl, o,p-dimethoxybenzyl, p-bromobenzhydryl, benzhydryl, triphenylmethyl, lower alkanoyl of 1–6 carbons or methoxymethyl; with a compound of the structure

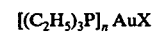

in which n is 1 or 2 and X is Cl, I, Br or, only when R is lower alkanoyl, (C₂H₅)₃PAuS— - in an inert aprotic organic solvent in which the reactants are soluble at from about room temperature up to the boiling point of the reaction mixture.

2. The method of claim 1 in which R is triphenylmethyl and X is chloro or bromo.

3. The method of claim 2 in which the solvent is methylene chloride.

4. The method of claim 1 in which R is acetyl, n is 1 and X is (C₂H₅)₃PAuS—.

5. The method of claim 4 in which the solvent is methylene chloride.

* * * * *

UNITED STATES PATENT AND TRADEMARK OFFICE
CERTIFICATE OF CORRECTION

PATENT NO. : 4,122,254

DATED : October 24, 1978

INVENTOR(S) : David T. Hill, Ivan Lantos and Blaine M. Sutton

It is certified that error appears in the above-identified patent and that said Letters Patent are hereby corrected as shown below:

Column 3, line 3, "2,3,4,6-Tetra-O-acetyl-L-S-trityl-L-" should read "2,3,4,6-Tetra-O-acetyl-1-S-trityl-1-"

line 6, "2,3,4,6-tetra-O-acetyl-L-" should read "2,3,4,6-tetra-O-acetyl-1-"

line 16, "2,3,4,6-tetra-O-acetyl-L-S-trityl-L-" should read "2,3,4,6-tetra-O-acetyl-1-S-trityl-1-"

line 20, "2,3,4,6-tetra-O-acetyl-L-S-trityl-L-" should read "2,3,4,6-tetra-O-acetyl-1-S-trityl-1-"

line 36, "2,3,4,6-Tetra-O-acetyl-L-S-trityl-L-" should read "2,3,4,6-Tetra-O-acetyl-1-S-trityl-1-"

UNITED STATES PATENT AND TRADEMARK OFFICE
CERTIFICATE OF CORRECTION

PATENT NO. : 4,122,254  
DATED : October 24, 1978  
INVENTOR(S) : David T. Hill, Ivan Lantos and Blaine M. Sutton It is certified that error appears in the above–identified patent and that said Letters Patent are hereby corrected as shown below:

Column 3, line 39, "2,3,4,6-tetra-O-acetyl-L-" should read "2,3,4,6-tetra-O-acetyl-1-"

line 49, "2,3,4,6-tetra-O-acetyl-D-S-trityl-L-" should read "2,3,4,6-tetra-O-acetyl-D-S-trityl-1-"

line 54, "acetyl-L-S-trityl-L-thio-β-D-glucopyranose" should read "acetyl-1-S-trityl-1-thio-β-D-glucopyranose"

line 59, "ra-O-acetyl-L-S-silver-L-thio-β-D-glucopyranose" should read "ra-O-acetyl-1-S-silver-1-thio-β-D-glucopyranose"

line 62, "2,3,4,6-tetra-O-acetyl-L-S-silver-L-thio-β-D-" should read "2,3,4,6-tetra-O-acetyl-1-S-silver-1-thio-β-D-"

UNITED STATES PATENT AND TRADEMARK OFFICE
CERTIFICATE OF CORRECTION

PATENT NO. : 4,122,254

DATED : October 24, 1978

INVENTOR(S) : David T. Hill, Ivan Lantos and Blaine M. Sutton

It is certified that error appears in the above-identified patent and that said Letters Patent are hereby corrected as shown below:

Column 4, line 11, "2,3,4,6-tetra-O-acetyl-L-S-acetyl-L-" should read "2,3,4,6-tetra-O-acetyl-1-S-acetyl-1-"

Signed and Sealed this

Fifth Day of June 1979

[SEAL]

Attest:

RUTH C. MASON
Attesting Officer

DONALD W. BANNER
Commissioner of Patents and Trademarks